US009523630B2

(12) United States Patent
Chen et al.

(10) Patent No.: US 9,523,630 B2
(45) Date of Patent: Dec. 20, 2016

(54) EMBEDDER HAVING MOBILE DISPENSER

(71) Applicant: Leica Microsystems Ltd. Shanghai, Shanghai (CN)

(72) Inventors: Ningjiang Chen, Shanghai (CN); Yuan Chu, Shanghai (CN); Chonglu Wang, Shanghai (CN)

(73) Assignee: Leica Microsystems Ltd. Shanghai, Shanghai (CN)

( * ) Notice: Subject to any disclaimer, the term of this patent is extended or adjusted under 35 U.S.C. 154(b) by 0 days.

(21) Appl. No.: 14/953,317

(22) Filed: Nov. 28, 2015

(65) Prior Publication Data

US 2016/0187237 A1 Jun. 30, 2016

(30) Foreign Application Priority Data

Dec. 29, 2014 (CN) .......................... 2014 1 0844094

(51) Int. Cl.
*A61B 10/00* (2006.01)
*G01N 1/36* (2006.01)
*B01L 3/02* (2006.01)

(52) U.S. Cl.
CPC ............... *G01N 1/36* (2013.01); *B01L 3/0203* (2013.01)

(58) Field of Classification Search
CPC .................................. A61B 10/00; G01N 1/36
See application file for complete search history.

(56) References Cited

U.S. PATENT DOCUMENTS

| 4,432,715 A * | 2/1984 | Ghim ................. A61C 13/0028 118/101 |
| 6,440,725 B1 * | 8/2002 | Pourahmadi ...... B01L 3/502715 422/547 |
| 8,486,351 B2 * | 7/2013 | Goerner ................... G01N 1/36 422/536 |
| 2008/0068707 A1 | 3/2008 | Goodman |

FOREIGN PATENT DOCUMENTS

| EP | 0138351 A2 | 4/1985 |
| EP | 2302350 A2 | 3/2011 |
| JP | 2001305025 A | 10/2001 |
| JP | 2002318177 A | 10/2002 |

* cited by examiner

*Primary Examiner* — Jyoti Nagpaul
(74) *Attorney, Agent, or Firm* — Hodgson Russ LLP (57) ABSTRACT

An embedder for embedding specimens in paraffin wax includes: a body having a paraffin reservoir for containing the paraffin wax; and a mobile dispenser disposed on the body, capable of being taken off from the body, and defining an inlet and an outlet, the inlet being communicated with the paraffin reservoir via a connecting tube so as to supply the paraffin wax in the paraffin reservoir to the mobile dispenser via the connecting tube, the mobile dispenser dispensing the paraffin wax via the outlet. With the embedder according to embodiments of the present invention, by means of the mobile dispenser detachably connected with the body, the embedder is flexible to use, convenient to operate, and high in efficiency.

17 Claims, 5 Drawing Sheets

EMBEDDER HAVING MOBILE DISPENSER

CROSS REFERENCE TO RELATED APPLICATIONS

This application claims priority of Chinese patent application number 201410844094.0 filed Dec. 29, 2014, the entire disclosure of which is incorporated by reference herein.

FIELD OF THE INVENTION

The present invention relates to an embedder for embedding specimens in paraffin wax, and more particularly to an embedder having a mobile dispenser.

BACKGROUND OF THE INVENTION

An embedder is a device for embedding specimens in paraffin wax. In the embedder in the related art, molten paraffin wax is released into a mold by means of a dispenser, so as to embed the specimens in the mold. The device for embedding specimens in paraffin wax generally has a dispenser for coating paraffin wax onto specimens. The dispenser of the embedder in the related art is fixed onto a body of the embedder and may not be separated from the body, such that the embedding of specimens can be only performed on a working stand of the embedder by only a single operator with a fixed embedding operation position and a low efficiency. Therefore, there is a need to improve the embedder.

SUMMARY OF THE INVENTION

Embodiments of the present invention seek to solve at least one of the problems existing in the related art to at least some extent. Accordingly, an embedder having a mobile dispenser is provided, in which the dispenser may be taken off (i.e. removed) from a body of the embedder, such that the embedder is flexible to use, convenient to operate, and high in efficiency.

An embedder for embedding specimens in paraffin wax according to an embodiment of the present invention includes: a body having a paraffin reservoir for containing the paraffin wax; and a mobile dispenser disposed on the body, capable of being removed from the body, and defining an inlet and an outlet, the inlet being communicated with the paraffin reservoir via a connecting tube so as to supply the paraffin wax in the paraffin reservoir to the mobile dispenser via the connecting tube, the mobile dispenser dispensing the paraffin wax via the outlet.

With the embedder according to embodiments of the present invention, by means of the mobile dispenser disposed on the body and capable of being removed from the body, the embedding operation may be conveniently performed, such that the embedder is flexible to use, convenient to operate, and high in efficiency.

In some embodiments, the connecting tube is a flexible tube.

In some embodiments, the mobile dispenser is communicated with the paraffin reservoir via the flexible tube when the mobile dispenser is taken off from the body.

In some embodiments, the flexible tube includes a flexible outer tube which is thermally insulating and electrically insulating, a flexible inner tube which is thermally conductive and electrically insulating and disposed in the flexible outer tube, and a heating wire disposed between the flexible outer tube and the flexible inner tube.

In some embodiments, the heating wire is spirally extended around the flexible inner tube.

In some embodiments, the mobile dispenser is disconnected from the connecting tube when the mobile dispenser is taken off from the body.

In some embodiments, the mobile dispenser has an adjusting member for adjusting a flow rate of the paraffin wax flowing out from the outlet.

In some embodiments, the mobile dispenser has an on-off valve connected between the inlet and the outlet and a control knob for controlling the on-off valve.

In some embodiments, the mobile dispenser has a display element for displaying a temperature and/or a volume of the paraffin wax contained within the mobile dispenser.

In some embodiments, the mobile dispenser has a heater for heating the paraffin wax contained therein.

In some embodiments, the mobile dispenser further has a rechargeable battery for supplying power to the heater.

In some embodiments, the embedder further comprises a charger disposed in the body for the rechargeable battery.

In some embodiments, the mobile dispenser is a dispensing gun having a trigger switch for opening the outlet and adjusting the flow rate of the paraffin wax flowing out from the outlet, and a gun holder is disposed on the body for placing the mobile dispenser thereon.

In some embodiments, the embedder further includes a fixed dispenser, wherein the body further includes a working stand, the fixed dispenser is fixed on the body and located above an operation surface of the working stand, and the fixed dispenser defines an inlet communicated with the paraffin reservoir and an outlet opposite to the operation surface.

In some embodiments, the body further includes a working stand, and the mobile dispenser is located above an operation surface of the working stand and the outlet is opposite to the operation surface when the mobile dispenser is placed onto the body.

In some embodiments, a heated working plate and a cooling plate are disposed on the operation surface, a collection container is disposed in the working stand, a guide channel is formed in the heated working plate, and guide through holes are formed in the guide channel for guiding the paraffin wax overflowing onto the heated working plate into the collection container.

In some embodiments, a tray and a forcep supporting stage are disposed on the working stand, and a ceramic coating is formed on at least one of an inner wall surface of the tray, a surface of the forcep supporting stage, a surface of the heated working plate, and a surface of the cooling plate.

REFERENCE NUMERALS 1 embedder
11 body
111 working stand
112 heated working plate
113 cooling plate
114 tray
115 forcep supporting stage
116 guide channel
117 collection container
118 operation surface
12 mobile dispenser
121 inlet
122 outlet
123 control knob
124 adjusting member
13 connecting tube
131 flexible outer tube
132 flexible inner tube
133 heating wire
14 another mounting position of mobile dispenser
15 yet another mounting position of mobile dispenser
16 gun holder
17 trigger switch

DETAILED DESCRIPTION OF THE INVENTION

Reference will be made in detail to embodiments of the present invention. The embodiments described herein with reference to drawings are explanatory, illustrative, and used to generally understand the present invention. The embodiments shall not be construed to limit the present invention.

As shown in FIGS. 1-5, an embedder 1 for embedding specimens in paraffin wax includes a body 11 and a mobile dispenser 12.

The body 11 has a paraffin reservoir for containing the paraffin wax. The paraffin reservoir may be a separate container mounted on the body 11, or a chamber formed in the body 11.

The mobile dispenser 12 is disposed on the body 11 and can be taken off from the body 11. The mobile dispenser 12 has an inlet 121 and an outlet 122. The inlet 121 is communicated with the paraffin reservoir via a connecting tube 13, so that the paraffin wax in the paraffin reservoir is supplied to the mobile dispenser 12 via the connecting tube 13. The mobile dispenser 12 dispenses the paraffin wax via the outlet 122, for example, the mobile dispenser 12 dispenses the paraffin wax into a mold containing a specimen therein.

It would be appreciated that, "mobile" means that the mobile dispenser 12 can be placed or mounted onto the body 11, and can be removed from the body 11. When the mobile dispenser 12 is taken off from the body 11, the mobile dispenser 12 may be still connected with the paraffin reservoir via the connecting tube 13, alternatively, the mobile dispenser 12 may be completely separated from the body 11 (i.e. the mobile dispenser 12 is disconnected from the connecting tube 13). Certainly, when the mobile dispenser 12 is taken off from the body 11, the paraffin wax may be dispensed onto a specimen (e.g., a specimen contained in a mold) for embedding the specimen. Preferably, when the mobile dispenser 12 is placed or mounted onto the body 11, the paraffin wax may be dispensed by the mobile dispenser 12 onto the specimen contained in the mold, at this time, the mobile dispenser 12 is used as a fixed dispenser. Alternatively, when the mobile dispenser 12 is placed or mounted onto the body 11, the mobile dispenser 12 may not be used to embed the specimen, and the body 11 is only used as a support for placing the mobile dispenser 12 thereon, and used to supply the paraffin wax to the mobile dispenser 12.

It would be appreciated that, when the mobile dispenser 12 is taken off from the body 11 and still connected with the paraffin reservoir via the connecting tube 13, the paraffin wax may be supplied to the mobile dispenser 12 from the paraffin reservoir via the connecting tube 13. When the mobile dispenser 12 is taken off from the body 11 and disconnected from the connecting tube 13 (i.e. the mobile dispenser 12 is completely separated from the body 11), the mobile dispenser 12 has a temporary storage chamber for storing the paraffin wax temporarily, such that the paraffin wax in the temporary storage chamber can be dispensed onto the specimen during the embedding.

With the embedder 1 according to embodiments of the present invention, the mobile dispenser 12 may be mounted onto the body 11 or removed from the body 11, such that the embedder 1 is flexible to use and convenient to operate.

The embedder according to a specific embodiment of the present invention will be described below with reference to FIGS. 1-2.

Figure 1:
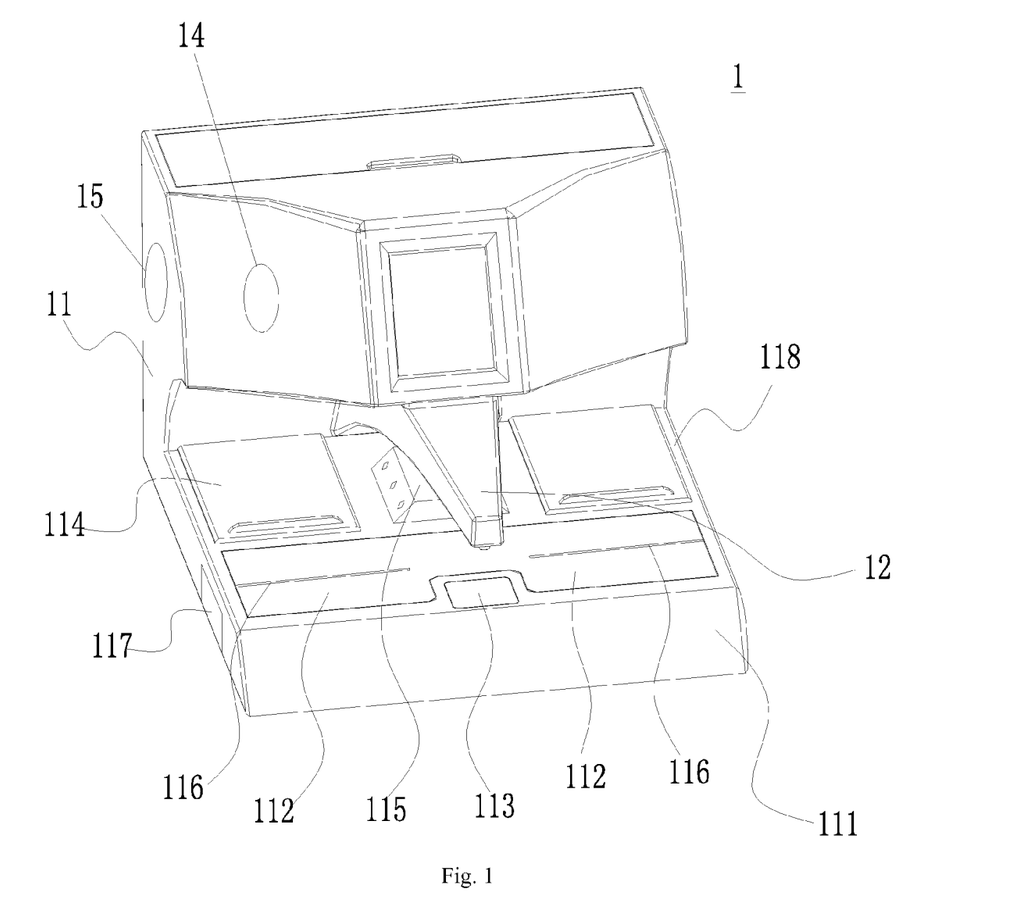
FIG. 1 is a schematic view of an embedder according to an embodiment of the present invention.

As shown in FIG. 1, the embedder according to the specific embodiment of the present invention includes a body 11 and a mobile dispenser 12.

The body 11 has a working stand 111 and an extension portion extending upwardly from a rear portion of the working stand 111, and the extension portion has a paraffin reservoir therein.

The mobile dispenser 12 has an inlet 121 and an outlet 122. The inlet 121 is communicated with the paraffin reservoir via a connecting tube 13, and the connecting tube 13 is preferably a flexible tube. The mobile dispenser 12 may be mounted onto the body 11, or may be taken off from the body 11.

As shown in FIG. 1, when the mobile dispenser 12 is mounted onto the body 11, the mobile dispenser 12 is located above the working stand 111, and the outlet 122 is opposed to an operation surface 118 of the working stand 111. At this time, the specimens placed on the working stand 111 may be embedded by means of the mobile dispenser 12.

Figure 2:
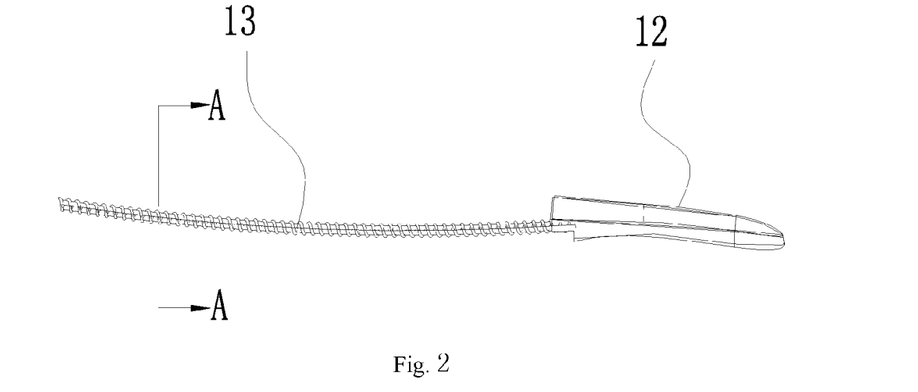
FIG. 2 is a schematic view showing that a mobile dispenser of the embedder in FIG. 1 is removed from a body of the embedder.

As shown in FIG. 2, when the mobile dispenser 12 is taken off from the body 11, the flexible connecting tube 13 is drawn out of the body 11, and the mobile dispenser 12 is still communicated with the paraffin reservoir via the flexible connecting tube 13. At this time, the mobile dispenser 12 may be held by hand to embed the specimens.

As shown in FIG. 1, the mobile dispenser may also be placed at a position 14 and/or a position 15 of the body 11. When the mobile dispenser is placed at the position 14 and/or the position 15 of the body 11, the mobile dispenser may not be used to perform the embedding. If the embedding needs to be performed, the mobile dispenser needs to be taken down from the position 14 and/or the position 15.

In other words, a plurality of mobile dispensers may be disposed on the body 11, some mobile dispensers may be used for embedding the specimens only when taken off from the body 11, and the other mobile dispensers (e.g., the mobile dispenser 12 in FIG. 1) may be used for embedding the specimens when taken off from the body 11 or mounted on the body 11.

In some embodiments, as shown in FIG. 1, a heated working plate 112 and a cooling plate 113 are disposed on the working stand 111. A collection container 117 is disposed in the working stand 111 for collecting the paraffin wax overflowing onto the working stand 111.

A guide channel 116 is formed in the heated working plate 112, and guide through holes (not shown) are formed in the guide channel 116 for guiding the paraffin wax overflowing onto the heated working plate 112 into the collection container 117. During embedding, the paraffin wax overflowing onto the heated working plate 112 flows into the collection container 117 via the guide channel 116 and the guide through holes. The collection container 117 may be pushed into or pulled out of the working stand 111, for example, the collection container 117 may be configured like a drawer.

A tray 114 and a forcep supporting stage 115 are also disposed on the working stand 111. A tray lid is disposed on the tray 114. The cassettes and molds for embedding may be placed in the tray 114. Forceps for clamping the cassettes, molds, and specimens may be placed on the forcep supporting stage 115, such that the forceps are convenient to use.

Preferably, a ceramic coating is formed on at least one of an inner wall surface of the tray 114, a surface of the forcep supporting stage 115, a surface of the heated working plate 112, and a surface of the cooling plate 113. More preferably, the ceramic coating may be formed on all the above surfaces. By forming the ceramic coating, it is possible to avoid scratching these surfaces when removing solidified paraffin wax thereon, and the paraffin wax is convenient to clean, thus increasing the life of the above components.

Figure 5:
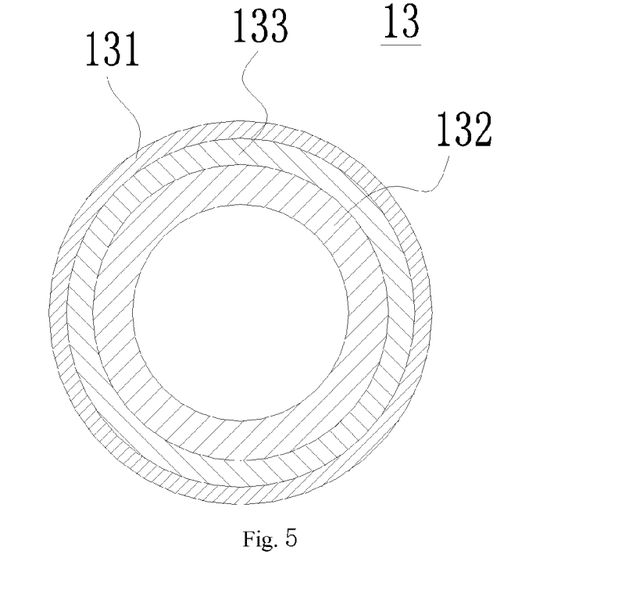
FIG. 5 is a sectional view of a flexible tube shown in FIG. 2 along a direction of A-A.

As shown in FIGS. 2 and 5, when the mobile dispenser 12 is taken off from the body 11, the mobile dispenser 12 is still communicated with the paraffin reservoir via the flexible connecting tube 13. The flexible connecting tube 13 includes a flexible outer tube 131 which is thermally insulating and electrically insulating, a flexible inner tube 132 which is thermally conductive and electrically insulating and disposed in the flexible outer tube 131, and a heating wire 133 disposed between the flexible outer tube 131 and the flexible inner tube 132. By means of the heating wire 133, the paraffin wax is heated when flowing through the flexible tube, thus ensuring the temperature and flowability of the paraffin wax without influencing the embedding effect.

Preferably, the heating wire 133 is spirally extended around the flexible inner tube 132, such that the paraffin wax is more evenly heated in the connecting tube 13.

The connecting tube 13 may be a hose with flexibility or without flexibility. The body 11 may have a space for containing the flexible connecting tube 13.

As shown in FIG. 1, when the embedding of the specimens is performed on the working stand 111, the mobile dispenser 12 is mounted onto the body 11, and the outlet 122 of the mobile dispenser 12 is opposed to the heated working plate 112 on the operation surface 118 of the working stand 111, such that the paraffin wax is dispensed onto the specimens on the heated working plate 112.

As shown in FIG. 2, when the embedding of the specimens is not suitable to be performed on the working stand 111, the mobile dispenser 12 is taken off from the body 11, such that the flexible connecting tube 13 is drawn out of the body 11. The mobile dispenser 12 is pulled to a position at which the specimens are to be embedded, and the liquid paraffin wax flows to the mobile dispenser 12 from the paraffin reservoir via the connecting tube 13, then is dispensed into the molds containing the specimens from the outlet 122 of the mobile dispenser 12.

The operation of the embedder according to the above embodiment of the present invention will be simply described below.

When the specimen is needed to be embedded, the cassette is taken out of the tray 114 using forceps placed on the forcep supporting stage 115, and a cassette cover is removed from a cassette body to open the cassette. Then, the mold with a suitable size is selected and placed on the heated working plate 112 below the outlet 122 of the mobile dispenser 12, and liquid paraffin wax in the paraffin reservoir is dispensed into the mold, preferably the filling volume of the paraffin wax into the mold is ¼ of a capacity of the mold. Next, the specimen is placed in the paraffin wax contained in the mold using forceps, and then the cassette body is placed on a top of the mold. Next, the mold is placed on the heated working plate 112 below the outlet 122 of the mobile dispenser 12 again, so that the liquid paraffin wax in the paraffin reservoir is filled into the mold containing the cassette body and the specimen. After that, the mold is moved onto the cooling plate 15 for cooling the liquid paraffin wax, after the liquid paraffin wax is solidified to be a paraffin wax block, the paraffin wax block containing the specimen and the cassette body fixed with the paraffin wax block are taken out of the mold. Finally, the paraffin wax block is trimmed excess paraffin wax from all edges of the cassette body, and the operation of the embedder according to the present invention is accomplished.

The paraffin wax overflowing onto the heated working plate 112 from the mold flows into the collection container 117 via the guide channel 116 and the guide through holes in the guide channel 116. When the solidified paraffin wax on the embedder needs to be cleaned, for example, the solidified paraffin wax in the tray 114 needs to be cleaned, the solidified paraffin wax may be scraped off by means of an instrument. Since the inner wall surface of the tray 114 is formed with the ceramic coating, the surface of the tray 114 will not be scratched, thus increasing the life of the tray, and the paraffin wax is convenient to clean.

When the mold is not suitable to be placed on the working stand 111 for embedding, the mobile dispenser 12 is taken off from the body 11 and moved to a position at which the mold containing specimens therein is placed, thus performing embedding. During embedding, the connecting tube 13 is heated by the heating wire 133, thus maintaining the flowability of the paraffin wax and the embedding effect. After finishing the embedding, the mobile dispenser 12 is placed back onto the body 11.

Figure 3:
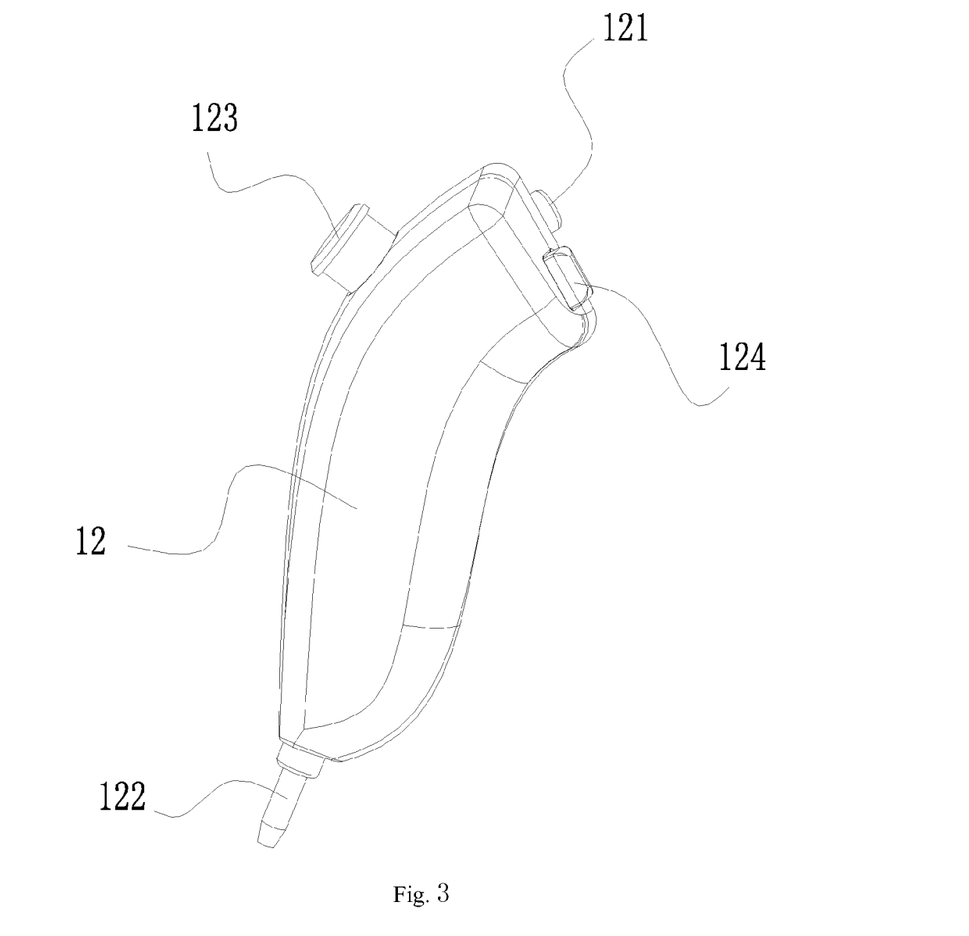
FIG. 3 is a schematic view showing that a mobile dispenser of an embedder is taken off from a body of the embedder according to one embodiment of the present invention.

FIG. 3 shows one example of mobile dispenser 12. As shown in FIG. 3, the mobile dispenser 12 is provided with an on-off valve (not shown) connected between the inlet 121 and the outlet 122 and a control knob 123 for controlling the on-off valve. The on-off valve may be turned on or off by operating the control knob 123, such that the inlet 121 may be communicated with or interrupted from the outlet 122. The mobile dispenser 12 also has an adjusting member 124, e.g., an adjusting knob or wheel, for adjusting the flow rate of the paraffin wax flowing out from the outlet 122.

Figure 4:
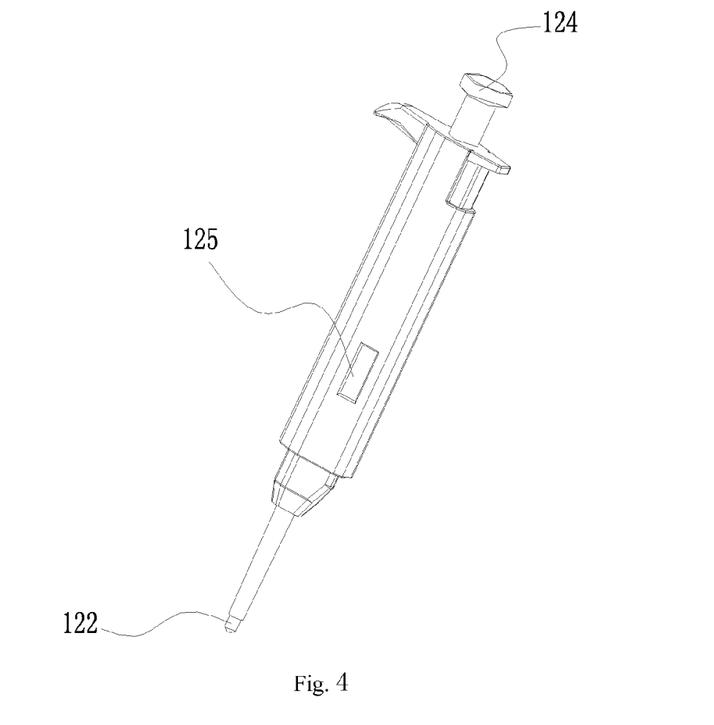
FIG. 4 is a schematic view showing that a mobile dispenser of an embedder is removed from a body of the embedder according to another embodiment of the present invention.

FIG. 4 shows another example of mobile dispenser 12. As shown in FIG. 4, the mobile dispenser 12 is configured as a pipette type dispenser provided with a display element 125. The display element 125 displays a temperature and/or a volume of the paraffin wax contained within the mobile dispenser 12, so that the operator can observe the current information of the paraffin wax contained within the mobile dispenser 12 at any time. The rest configurations and structures of the mobile dispenser 12 as shown in FIG. 4 can refer to corresponding configurations and structures of the mobile dispenser 12 as shown in FIG. 4.

In the embodiment shown in FIG. 3 and FIG. 4, the mobile dispenser 12 may have a temporary storage chamber for storing the paraffin wax temporarily, such that the mobile dispenser 12 may be completely separated from the body 11, i.e. disconnected from the connecting tube 13, when mobile dispenser 12 is taken off from the body 11. At this time, the connecting tube 13 may be a flexible tube or a rigid tube, and an on-off valve may be disposed at the connecting tube 13. When the mobile dispenser 12 is placed on the body 11, the inlet 121 is communicated with the connecting tube 13. The on-off valve is turned on, and the paraffin wax in the paraffin reservoir enters the temporary storage chamber in the mobile dispenser 12. When the mobile dispenser 12 is to be removed from the body 11, the on-off valve is turned off, then the mobile dispenser 12 is taken off. The inlet 121 is disconnected from the connecting tube 13, then the mobile dispenser 12 may be held by the operator for embedding the specimens, such that the embedder may be more flexible and convenient to use.

Moreover, in order to prevent a temperature of the paraffin wax stored in the temporary storage chamber from decreasing, especially when the mobile dispenser 12 is separated from the body 11, the mobile dispenser 12 as shown in FIG. 3 or FIG. 4 may have a heater for heating the paraffin wax contained in the temporary storage chamber and a rechargeable battery for supplying power to the heater. One the other hand, the embedder may have a charger for the rechargeable battery disposed in the body 11, for example the charger may be disposed in the position 14 and/or the position 15. So that the rechargeable battery of the mobile dispenser 12 can be recharged when the mobile dispenser 12 is placed at the position 14 and/or the position 15, thus, the heater of the mobile dispenser 12 can be worked continually and stably.

In some embodiments, the embedder 1 further includes a fixed dispenser (not shown), which is fixed on the body 11, and cannot be taken off from the body 11 for embedding. The term "fixed" used herein means that the dispenser cannot be used to embed the specimens when taken off from the body 11, but may be detachably mounted on the body 11. For example, the fixed dispenser may be fixed at a position shown by the mobile dispenser 12, and the mobile dispenser 12 may be placed at the position 14 and/or the position 15. The fixed dispenser is located above the operation surface 118 of the working stand 111, an inlet of the fixed dispenser is communicated with the paraffin reservoir, and an outlet of the fixed dispenser is opposed to the operation surface 118.

As described above, in FIG. 1, the mobile dispenser 12 may be used for embedding the specimens when mounted on the body 11. Therefore, the mobile dispenser 12 also has the function of the fixed dispenser. In other words, the mobile dispenser and the fixed dispenser is the same dispenser.

By providing the fixed dispenser, the flexibility of the embedding operation is further enhanced. Moreover, the embedding operations by means of the fixed dispenser and the mobile dispenser do not influence each other, thus enhancing the efficiency.

The embedder 1 according to another embodiment of the present invention will be described below with reference to FIGS. 6-7.

Figure 6:
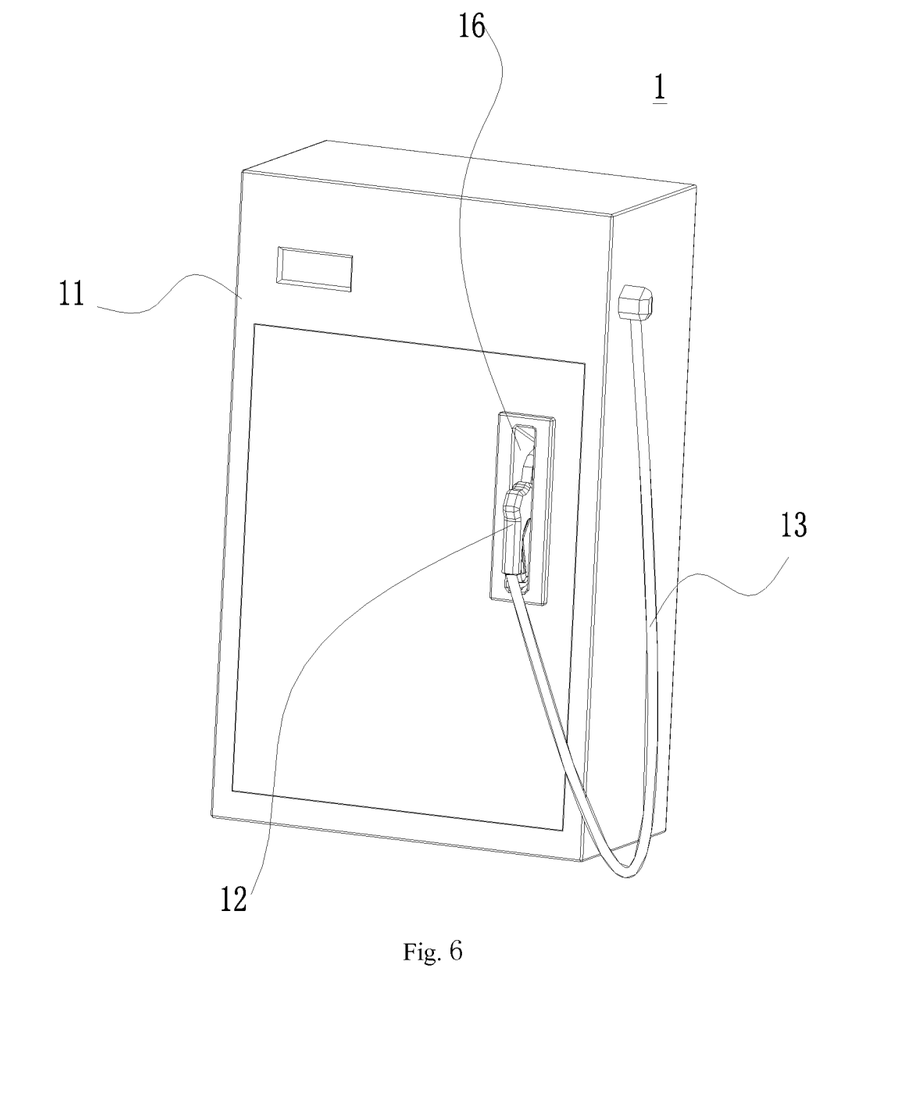
FIG. 6 is a schematic view of an embedder according to another embodiment of the present invention.
Figure 7:
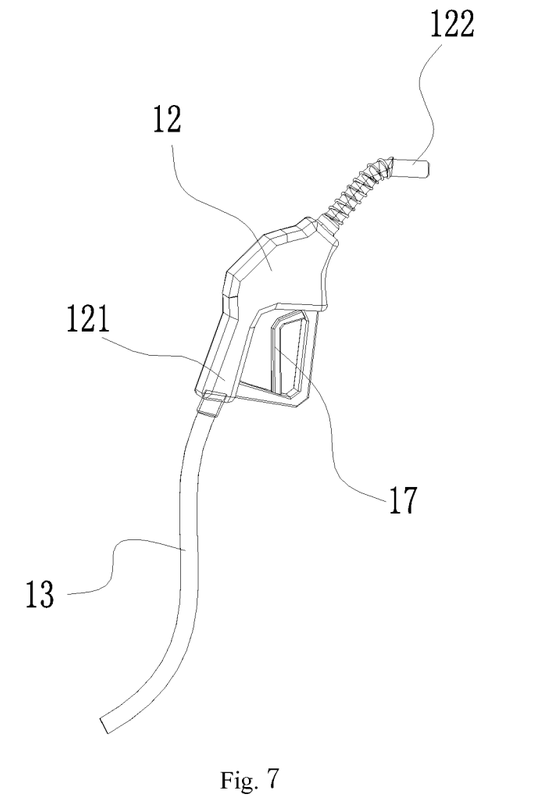
FIG. 7 is a schematic view of a mobile dispenser of the embedder shown in FIG. 6.

As shown in FIGS. 6-7, the body 11 of the embedder 1 is a cabinet body, the mobile dispenser 12 is configured as a dispensing gun, and a gun holder 16 is disposed on the body 11 for placing the mobile dispenser 12 thereon.

The dispensing gun is communicated with the paraffin reservoir via the connecting tube 13. The dispensing gun has a trigger switch 17. The trigger switch 17 may be used for communicating the inlet 121 with the outlet 122 or disconnecting the inlet 121 from the outlet 122, and may also be used as the adjusting member for adjusting the flow rate of the paraffin wax flowing out from the outlet 122. After the embedding is completed, the trigger switch 17 is released, and the dispensing gun is placed back onto the gun holder 16.

With the embedder according to embodiments of the present invention, by means of the mobile dispenser, the use convenience and working efficiency are enhanced, and the embedder is applied to the embedding of large-size specimens.

In the present invention, unless specified or limited otherwise, the terms "mounted," "connected," "coupled," "fixed" and the like are used broadly, and may be, for example, fixed connections, detachable connections, or integral connections; may also be mechanical or electrical connections; may also be direct connections or indirect connections via intervening structures; may also be inner communications of two elements, which can be understood by those skilled in the art according to specific situations.

In the present invention, unless specified or limited otherwise, a structure in which a first feature is "on" or "below" a second feature may include an embodiment in which the first feature is in direct contact with the second feature, and may also include an embodiment in which the first feature and the second feature are not in direct contact with each other, but are contacted via an additional feature formed therebetween. Furthermore, a first feature "on," "above," or "on top of" a second feature may include an embodiment in which the first feature is right or obliquely "on," "above," or "on top of" the second feature, or just means that the first feature is at a height higher than that of the second feature; while a first feature "below," "under," or "on bottom of" a second feature may include an embodiment in which the first feature is right or obliquely "below," "under," or "on bottom of" the second feature, or just means that the first feature is at a height lower than that of the second feature.

Reference throughout this specification to "an embodiment," "some embodiments," "one embodiment", "another example," "an example," "a specific example," or "some examples," means that a particular feature, structure, material, or characteristic described in connection with the embodiment or example is included in at least one embodiment or example of the present invention. Thus, the appearances of the phrases such as "in some embodiments," "in one embodiment", "in an embodiment", "in another example," "in an example," "in a specific example," or "in some examples," in various places throughout this specification are not necessarily referring to the same embodiment or example of the present invention. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present invention, and changes, alternatives, and modifications can be made in the embodiments without departing from spirit, principles and scope of the present invention.

What is claimed is:

1. An embedder for embedding specimens in paraffin wax, comprising:
    a body having a paraffin reservoir for containing the paraffin wax; and
    a mobile dispenser removably disposed on the body, the mobile dispenser defining an inlet and an outlet, the inlet communicating with the paraffin reservoir via a connecting tube so as to supply the paraffin wax in the paraffin reservoir to the mobile dispenser via the connecting tube, the mobile dispenser dispensing the paraffin wax via the outlet, wherein the connecting tube is a flexible tube, and wherein the flexible tube comprises a flexible outer tube which is thermally insulating and electrically insulating, a flexible inner tube which is thermally conductive and electrically insulating and disposed in the flexible outer tube, and a heating wire disposed between the flexible outer tube and the flexible inner tube.

2. The embedder according to claim 1, wherein the mobile dispenser communicates with the paraffin reservoir via the flexible tube when the mobile dispenser is removed from the body.

3. The embedder according to claim 1, wherein the heating wire extends spirally around the flexible inner tube.

4. The embedder according to claim 1, wherein the mobile dispenser is disconnected from the connecting tube when the mobile dispenser is removed from the body.

5. The embedder according to claim 1, wherein the mobile dispenser has an adjusting member for adjusting a flow rate of the paraffin wax dispensed from the outlet.

6. The embedder according to claim 1, wherein the mobile dispenser has an on-off valve connected between the inlet and the outlet and a control knob for controlling the on-off valve.

7. The embedder according to claim 1, wherein the mobile dispenser has a display element for displaying a temperature and/or a volume of the paraffin wax contained within the mobile dispenser.

8. The embedder according to claim 1, wherein the mobile dispenser has a heater for heating the paraffin wax contained therein.

9. The embedder according to claim 8, wherein the mobile dispenser further has a rechargeable battery for supplying power to the heater.

10. The embedder according to claim 9, further comprising a charger disposed in the body for the rechargeable battery.

11. The embedder according to claim 1, wherein the mobile dispenser is a dispensing gun having a trigger switch for opening the outlet and adjusting the flow rate of the paraffin wax dispensed from the outlet, and a gun holder is disposed on the body for placing the mobile dispenser thereon.

12. The embedder according to claim 1, further comprising a fixed dispenser, wherein the body further comprises a working stand, the fixed dispenser is fixed on the body and located above an operation surface of the working stand, and the fixed dispenser defines an inlet communicating with the paraffin reservoir and an outlet opposite to the operation surface.

13. The embedder according to claim 12, wherein a heated working plate and a cooling plate are disposed on the operation surface, a collection container is disposed in the working stand, a guide channel is formed in the heated working plate, and guide through holes are formed in the guide channel for guiding the paraffin wax overflowing onto the heated working plate into the collection container.

14. The embedder according to claim 13, wherein a tray and a forcep supporting stage are disposed on the working stand, and a ceramic coating is formed on at least one of an inner wall surface of the tray, a surface of the forcep supporting stage, a surface of the heated working plate, and a surface of the cooling plate.

15. The embedder according to claim 1, wherein the body further comprises a working stand, and the mobile dispenser is located above an operation surface of the working stand and the outlet is opposite to the operation surface when the mobile dispenser is placed onto the body.

16. The embedder according to claim 15, wherein a heated working plate and a cooling plate are disposed on the operation surface, a collection container is disposed in the working stand, a guide channel is formed in the heated working plate, and guide through holes are formed in the guide channel for guiding the paraffin wax overflowing onto the heated working plate into the collection container.

17. The embedder according to claim 16, wherein a tray and a forcep supporting stage are disposed on the working stand, and a ceramic coating is formed on at least one of an inner wall surface of the tray, a surface of the forcep supporting stage, a surface of the heated working plate, and a surface of the cooling plate.

* * * * *